United States Patent

Pritsos et al.

[11] Patent Number: 5,888,532
[45] Date of Patent: Mar. 30, 1999

[54] TREATMENT OF ALCOHOLISM AND RELATED DISORDERS WITH (NICOTINAMIDE-ADENINE DINUCLEOTIDE) PHOSPHATE DERIVATIVES

[76] Inventors: Chris A. Pritsos, 921 Lionel Ct., Sparks, Nev. 89434; Alcinda Miller, 1113 Stanley Ave., N. Las Vegas, Nev. 89030

[21] Appl. No.: 912,084

[22] Filed: Aug. 15, 1997

Related U.S. Application Data

[60] Provisional application No. 60/024,078, Aug. 16, 1996.
[51] Int. Cl.⁶ ....................................... A61F 2/00
[52] U.S. Cl. ........................ 424/423; 424/423; 424/490; 424/465; 424/451; 424/456; 514/810; 514/811; 536/26.24
[58] Field of Search ..................... 424/423, 490, 424/465, 451, 456; 514/810, 811; 536/26.24

[56] References Cited

U.S. PATENT DOCUMENTS 5,773,423   6/1998   Jacobson et al. ................... 514/45

*Primary Examiner*—D. Gabrielle Brouillette
*Assistant Examiner*—Lakshmi Channavajjala
*Attorney, Agent, or Firm*—Skinner, Sutton & Watson; Charles Hartman

[57] ABSTRACT

Alcoholic addiction is treated by administering pyridine nucleotide phosphate derivatives having the formula represented by Formula 1:

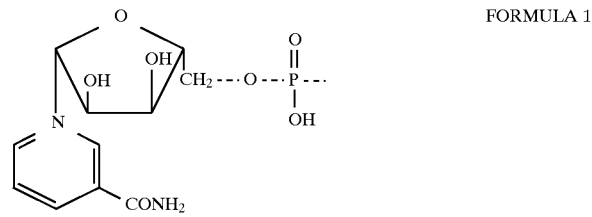

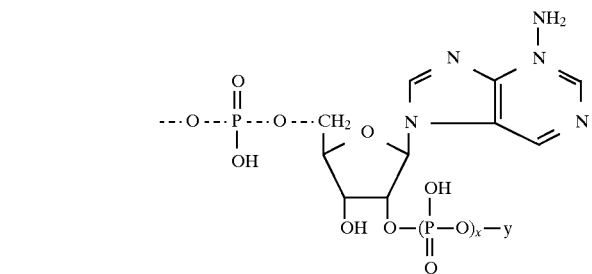

where y can be a second NAD group or an adenosine group and x can be 1, 2, or 3.

14 Claims, No Drawings ns and are

TREATMENT OF ALCOHOLISM AND RELATED DISORDERS WITH (NICOTINAMIDE-ADENINE DINUCLEOTIDE) PHOSPHATE DERIVATIVES

This application claims benefit of provisional application Ser. No. 60/024,078, filed Aug. 16, 1996.

BACKGROUND OF THE INVENTION

1. Field of the Invention

This invention relates to treatments of addictive disorders, such as alcoholism, more particularly this invention relates to the treatment of the symptoms of alcoholic withdrawal.

2. State of the Art

Alcoholism is a common health problem in the United States. Millions suffer from the disease in one degree or another. The results of the disease are billions of dollars spent on treatment, rehabilitation, and more billions wasted on lost man hours at work and petty crimes committed by inebriated individuals. The social cost to the families and acquaintances of alcoholics is incalculable.

Alcoholism is a syndrome consisting of 2 phases: problem drinking and alcohol addiction. Problem drinking is the repetitive use of alcohol, often to alleviate anxiety or solve other emotional problems. Alcohol addiction is a true addiction similar to that which occurs following the repeated use of other sedative-hypnotics.

40% of Japanese have aldehyde dehydrogenase deficiency and are more susceptible to the effects of alcohol.

The signs of alcoholic intoxication are the same as those of overdosage with any other central nervous system depressant: drowsiness, errors of commission, psyomotor dysfunction, disinhibition, dysarthia, ataxia, and nystagmus.

There is a wide spectrum of manifestations of alcoholic withdrawal, ranging from anxiety, decreased cognition, and tremulousness through increasing irritability and hyperactivity to full-blown delirium tremens. The latter is an acute organic psychosis that is usually manifested within 24–72 hours after the last drink (but may occur up to 7–10 days later). It is characterized by mental confusion, tremor, sensory hyperacuity, visual hallucinations (often of snakes, bugs, etc.), autonomic hyperactivity, diaphoresis, dehydration, electrolyte disturbances, hypokalemia hypomagnesemia, seizures and cardiovascular abnormalities. The acute withdrawal syndrome is often completely unexpected and occurs when the patient has been hospitalized for some unrelated problem and presents as a diagnostic problem. Suspect alcohol withdrawal in every unexplained delirium. Seizures occur early (the first 24 hours) and are more prevalent in persons who have a history of withdrawal syndromes. The mortality rate from delirium tremors has steadily decreased with early diagnosis and improved treatment.

In addition to the immediate withdrawal symptoms, there is evidence of persistent long-term one, including sleep disturbances, anxiety, depression, excitability, fatigue, and emotional volatility. These symptoms may persist for 3–12 months, and in some cases they become chronic.

Alcoholic (Organic) Hallucinosis occurs either during heavy drinking or on withdrawal and is characterized by a paranoid psychosis.

According to the National Institute on Alcohol Abuse and Alcoholism new treatments and new medical agents to help provide such new treatments are needed for the additional factors they have identified as effects of alcoholism including: 1) agents to decrease the desire to drink by attenuating alcohol craving and blocking the euphoric effect (reward) derived from drinking alcohol; 2) agents to induce sobriety in intoxicated individuals; 3) mechanisms of alcohol intoxication and development of a clinically useful antagonist of alcohol-intoxication. (A significant number of people die each year from alcohol overdoses. In order to effectively treat this problem, medications developed based on the mechanisms of the depressant effects of alcohol are needed); 4) development of medications to improve cognitive dysfunction in alcoholic dementia/Korsakoff's psychosis. (Progress in this area would lead to enrichment in quality of life of alcoholics as well as reduction in costs of long-term institutionalization. Recent studies have shown that serotonin reuptake inhibitors can improve memory to a clinically meaningful degree in some patients with alcohol-induced amnesia); 5) development of medications to treat alcoholic liver disease and other alcohol related, end-organ diseases. (In reducing the high mortality from alcoholic hepatitis, potential medications include that affect the production or clearance of cytokines, prevent other causes of necrosis/inflammation, and avert the progression of fibrosis. Other potential agents are those with potential utility in treatment of portal hypertension and alcohol-induced pancreatic disease); 6) determination of appropriate medicational strategy based on severity of acute alcohol withdrawal; 7) mechanisms of alcohol dependence, Psychological and physical dependence on alcohol are presumed to contribute to continued drinking and relapse. (Understanding the cellular and molecular mechanisms of craving for alcohol after chronic use and how it might be reduced is needed); 8) strategies to reduce the organ damage caused by chronic alcohol abuse. (This damage is mostly to the liver, brain, cardiovascular system, and pancreas. Research is needed into the underlying mechanism of alcoholic hepatitis, brain damage portal hypertension, cardiomyopathy, and pancreatitis. Understanding these mechanisms will lead to the development of medications that are useful in alleviating or counter-acting alcohol induced tissue injury, such as free radical scavengers, cognitive enchanters, and transplantation). It is clear that new approaches to the treatment of alcoholism are needed.

There have been many approaches to the problem, including the psychological, such as counseling and self help programs such as Alcoholics Anonymous and drug treatment such as Antibuse. None have been completely successful either in stopping all alcoholics from drinking or from keeping a non-drinking alcoholic from starting to drink again.

One promising approach to the treatment of acute intoxication is the administration of Nicotinamide-adenine Dinucleotide (NAD), also known as Diphospho Pyridine Neucleotide (DPN) and Coenzyme I to the sufferer. This allows the alcohol dehydrogenase found throughout the cytoplasm to function to oxidize alcohol in other places in the body other than the liver.

The use of pyridine nucleotides is known to facilitate the treatment of several diverse diseases. For example, U.S. Pat. No. 3,412,190 to O'Holleran teaches the use of NAD for the lipids in the blood stream. They have also been used to treat alcoholism. Canadian Patent 670,909 teaches the use of NAD for the control the symptoms of acute alcoholism.

NAD is metabolized in the body rapidly. It would be advantageous to provide a slower metabolizing form of NAD for the recovering alcoholic. NAD also comes in a phosphated form, NADP having slightly different activity and resistance to metabolic deactivation. It would be advantageous to allow the alcoholic sufferer to be dosed with both NAD and NADP to increase the spectrum of the pharmacological action. Finally, NAD is not completely absorbed by the gastric acid intestinal mucosa. It would be advantageous to provide a form of completely absorbed NAD that could be orally administered.

SUMMARY OF THE INVENTION

This invention provides a new compound and a method for treating alcoholic addiction by administering pyridine nucleotide phosphate derivatives.

One aspect of this invention is a method of treating the symptoms of alcoholic withdrawal comprising:

administering to a patient in need of such treatment a pharmaceutically acceptable formulation of a medicament selected from the group consisting of compounds having the formula represented by Formula 1:

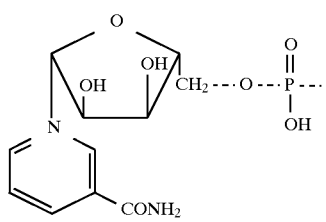

FORMULA 1

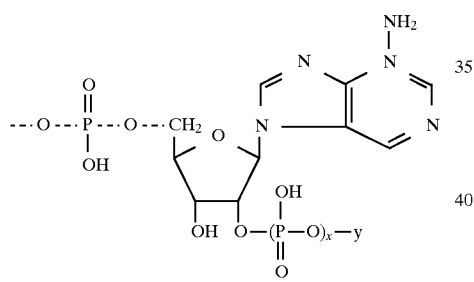

where y can be another group having the structure represented by Formula 2

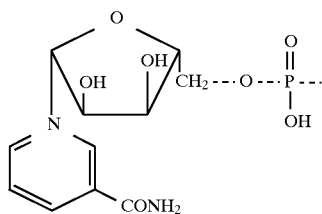

FORMULA 2

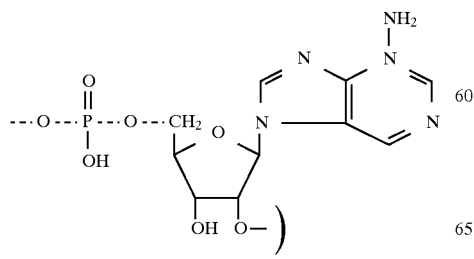

or a group having a structure represented by the structure of

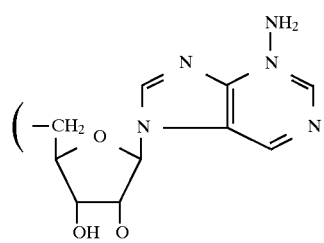

FORMULA 3 and x can be 1, 2, or 3.

Another aspect of this invention is the compound represented by formula 1.

DETAILED DESCRIPTION OF THE PREFERRED EMBODIMENT

Compounds having the represented by Formula 1:

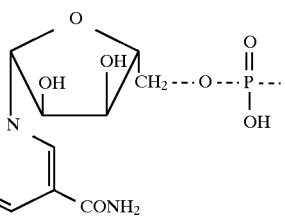

FORMULA 1

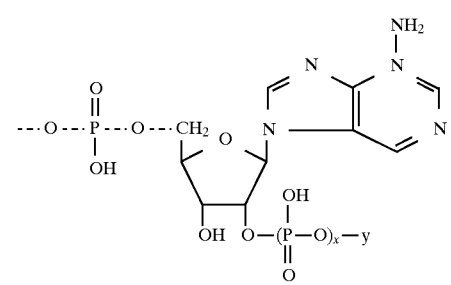

where y can be another group having the structure represented by Formula 2

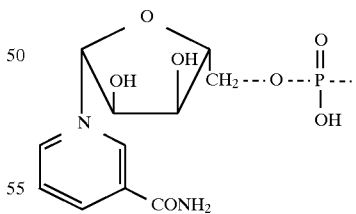

FORMULA 2

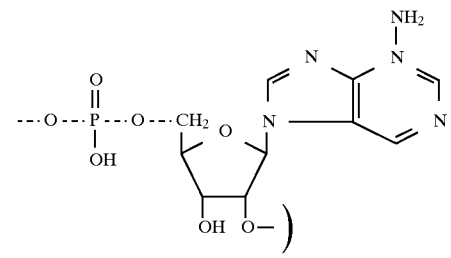

or a group having a structure represented by the structure of

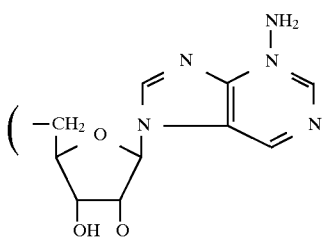

FORMULA 3 and x can be 1, 2, or 3.

The compounds formula 1 are administered to patients in need of treatment for alcoholism or for drug addiction, where the drugs are amphetamines, barbiturates, opiates, and similar drugs of abuse. Administration of the compounds of formula 1 while the patient is intoxicated reduce the effects of the intoxicating drug or alcohol, and administration of the compound of formula 1 after the patient has achieved sobriety tends to reduce the amount of craving for self administration of the drug or renewed drinking of alcohol. Tests for alcoholism include clinical tests such as SGOT, SGPT-liver enzyme tests, glutamyl transferase and mean corpuscular volume.

The compounds represented by the structure shown in Formula 1 are new. They are made by heating an acidic, preferably through $H_2SO_4$ solution, a polar solution of NAD, preferably an aqueous solution to between about 40° C. to 100° C., in the presence of NADP or a mono-, di-, or tri-phosphorated adenine molecule. The resultant product solution is purified by liquid chromatographic techniques well known in the art.

The compounds of the present invention have both acid functionality (on the phosphorous groups) and base functionality (the primary amine residue on the adenine). The compounds of the Formula 1 are used either as the free acids or salts of acceptable alkaline earth, alkali metal, and simple ammonium ions, where a simple ammonium ion is one of the form $NR_1R_2R_3R_4$, where $R_1$, $R_2$, $R_3$, and $R_4$ can be the same or different and can be any alkyl group having fewer than five carbon atoms, or hydrogen.

Such compounds can be brought into suitable galenic forms, such as formulations for oral, transdermal, or intranasal use, and for injection, or the like, in accordance with well known conventional pharmaceutical procedures. Such formulations comprise the active compound in association with pharmaceutically acceptable carriers. The carriers may be any inert material, organic or inorganic, suitable for percutaneous or parenteral administration, such as water, gelatin, gum arabicum, lactose, cellulose, starch, sodium starch glycolate, cyclodextrins, calcium hydrogen phosphate, magnesium stearate, talcum, colloidal silicon dioxide, stabilizers, wetting agents, emulsifiers, flavoring agents, buffers, and the like.

The compound can be formulated in a flexible closed capsule made of Silastic (a brand name for dimethylsiloxyane/copolymer). These can be inserted under the skin for long term slow release of the drug.

The pharmaceutical formulations according to the invention comprise solid as well as liquid dosage forms, such as tablets, capsules, powders, syrups, elixirs, sterile solutions, suspensions or emulsions, and other conventional formulations for oral and parenteral administration, and other conventional modes of administration including suppositories, throat lozenges or a potable patient residing device.

The dosage may be dispensed by the treating physician or by the patient. The administration may be on a regimen of single dosages or by controlled injection in the intervenious mode, by either adding to an on going drip or by a preprogramed electronic dosing machine.

The dosage of the compound of Formula I to be administered will, of course, depend on the potency of the selected specific compound, the mode of administration, the age and weight of the patient, the severity of the condition to be treated, and the like. The daily dosage may, for example, be from about 0.001 mg to about 25 mg per kilo of body weight, administered in one or more doses. The compositions of the invention are preferably formulated in a unit dosage form, containing, for example, about 0.05 to about 500 mg of the active ingredient. The preferred total daily dosage of the compound of formula 1 will be between about 0.5 and 5.0 grams per day, preferably between about 0.9 and 3.0 grams per day, and most preferably between about 1.0 to 2.0 grams per day.

Pharmaceutically acceptable refers to those properties or substances which are acceptable to the patient from a pharmacological or toxicological point of view and to the manufacturing pharmaceutical chemist from a physical or chemical point of view regarding composition, formulation, stability, patient acceptance and bioavailability.

When prepared in the form of tablets, the formulation requires that the active ingredient (a compound having of formula 1) is mixed with a pharmaceutical carrier such as gelatin, starch, lactose, magnesium stearate, talc, arabic gum, and the like. The tablets may be coated with sucrose or other appropriate materials including enteric coatings. They may be processed so that their dissolution rate in the stomach is extended or delayed beyond the rate that would be observed in uncoated materials. Finally, they might be coated to continuously release a predetermined amount of active principle.

A preparation in capsules may be easily obtained by mixing the active ingredient with a solid powdered or liquid diluent of acceptable sort and by using the mixture thereby obtained to fill either soft or hard gelatin capsules.

A preparation in the form of syrup or elixir, either to be administered as a liquid or as drops, contains the active ingredient; a sweetening agent, preferably an antiseptic such as acaloric, methylparaben and propylparaben; other flavoring agents in addition to the sweetening agent; and suitable coloring agent, all dissolved in an inert liquid vehicle.

Water-dispersible powders or granulates contain the active ingredient in admixture with dispersing or wetting agents, or with suspending agents such polyvinylpyrrolidone and the similar agents. Sweetening agents; flavoring agents; and similar optional agents may also be added to create an acceptable product for the consumer.

The active principle may also be formulated in the form of microcapsules or microemulsions optionally with one or more carriers or additives.

For oral administration, each unit dosage form may advantageously contain from 0.1 to 500 mg of active principle, preferably from 1.0 to 50.0 mg. Depending on the type of release rate, the desired number of pills that may be taken, and the like, unit dosage forms containing a higher amount of active principle may as well be envisaged.

For parenteral administration the pharmaceutical compositions according to the present invention will contain, in addition to the active principle, a mixture of one or more pharmaceutically acceptable, aqueous or non aqueous, sterile vehicles.

The above discussed pharmaceutical compositions may also contain some additives such as suitable stabilisers, wetting agents, emulsifyers, or dispersants. These compositions for parenteral administration may be sterilised by, for example, filtration through a finely pored membrane filter which removes microrganisms which may have gotten into the formulation (such as Millipore® filters) or by incorporation of various sterilizing agents to the compositions.

These compositions may also be prepared as solid formulations to be dissolved or suspended in sterile water or in another sterile injectable solvent before use.

For parenteral administration each unit dosage form may advantageously contain from 0.05 to 25 mg of active principle and preferably from 0.1 to 5 mg.

EXAMPLES

The following examples illustrate specific aspects of the preferred embodiment and are not intended to, nor should they be read as, limiting the scope of the invention disclosed herein and the claims appended hereto.

Example 1

This example shows one method to make the compound of Formula 1 wherein the substituent y is a second NAD unit and x is one.

One millimole of NAD is dissolved in water 1N in sulfuric acid. The mixture is heated to 50° C. and a solution containing 1 millimole of NADP added drop-wise with continuous stirring. The reaction is allowed to react for 30 minutes. The reaction mixture is them cooled and the product is separated by preparatory liquid chromatographic techniques.

Example 2

This example shows one method to make the compound of formula 1 wherein the substituent y is adenine and x is three.

One millimole of NAD is dissolved in water 1 N in sulfuric acid. The mixture is heated to 50° C. and an aqueous solution containing 1 millimole of ATP (adenosine triphosphate) added drop-wise with continuous stirring. The reaction mixture is allowed to stir for 30 minutes, then mixture is cooled and the product is separated by preparatory liquid chromatographic techniques.

Example 3

This example shows the preparation of the tablet form of the pharmaceutical preparation of this invention.

The table of ingredients is referred to in the following example.

| Ingredients | Mg/tablet |
|---|---|
| 1. Compound of formula 1 | 2.0 |
| 2. Cellulose, microcrystalline | 57.0 |
| 3. Calcium hydrogen phosphate | 15.0 |
| 4. Sodium starch glycolate | 5.0 |
| 5. Silicon dioxide, colloidal | 0.25 |
| 6. Magnesium stearate | 0.75 |
| | 80.0 mg |

The title compound of in Example 1 is mixed with ingredients 2, 3, 4 and 5 for about 10 minutes. The magnesium stearate is then added, the resultant mixture being mixed for about 5 minutes and then compressed into tablet form with. An enteric coating is then added.

Example 4

This example shows the preparation of the tablet form of the pharmaceutical preparation of this invention.

| Ingredients | Mg/tablet |
|---|---|
| 1. Compound in Ex. 21 | 2 |
| 2. Lactose | 186 |
| 3. Corn Starch | 20 |
| 4. Talc | 15 |
| 5. Magnesium stearate | 2 |
| | 225 mg |

The title compound in Example 1 is mixed with ingredients 2 and 3 and then milled. The resulting mixture is mixed with ingredients 4 and 5 and then filled into capsules of appropriate size.

Example 5

This example shows the method of treating a sufferer of alcoholism using an intravenous administration of the compound of formula 1.

A subject is given 200 ml of 96% ethyl alcohol, (equal to between about 12 and 15 one-ounce glasses of grain neutral spirits cut to 100 proof). Clinical intoxication is determined and blood alcohol level peaks. Then the compound of Formula 1 in sterile saline solution is administered intravenously. The client may experience pain in the back of the neck, parethesias at the base of the tongue, dizziness and nausea or other well known reactions to NAD. The rate of administration is reduced to eliminate these symptoms, and increased to reduce the symptoms of drunkenness. Usually, within three minutes or so after cessation of administration of the compound of formula 1, the client returns to his previous level of intoxication.

With continued administration of the appropriate dosage of the compound of Formula 1 symptoms of inebriation will nearly disappear after six hours. The subject will experience none of the symptoms of headache, nervousness or nausea (i.e., hangover) normally to be expected after ingesting the amount of ethanol consumed. Additionally, administration of the compound of Formula 1 reduces the craving and desire for alcohol normally to be expected after such an episode of inebriation. Sleep the night after the treatment will be normal and without any need of additional alcohol or other sleep inducing agents during the night to achieve sleep.

Example 6

This Example shows the treatment of a patient with an oral dosage form.

An inebriated sufferer of alcoholism presented to the treating physician is given the medicament described in Example 3, one pill every ten minutes. The symptoms of acute inebriation subside after the first several minutes of administration. The Pills are continued until the patient can go for at least one half hour with out the administration of the pills and still remain sober.

Example 7

This Example shows the treatment of a patient suffering from drug addiction with an oral dosage form.

An intoxicated sufferer of drug abuse presented to the treating physician is given the medicament described in Example 3, one pill every ten minutes. The symptoms of acute drug intoxication subside several minutes after the first administration of the pill. The pills are continued until the patient can go for at least one half hour without the administration of the pills and still remain sober. The administration of the pills reduce the craving for additional amounts of the addicting drug.

The Invention has been described in terms of reference to specific embodiments and examples. Alternative embodiments will suggest themselves to those skilled in the art. The appended claims are intended to encompass all such alternative embodiments.

We claim:

1. A method of treating the symptoms of alcoholic withdrawal comprising:

administering to a patient in need of such treatment a pharmaceutically acceptable formulation of a medicament selected from the group consisting of compounds having the formula represented by Formula 1:

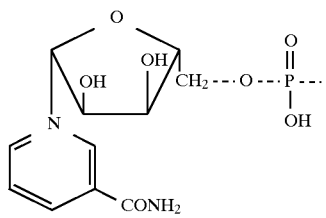
FORMULA 1

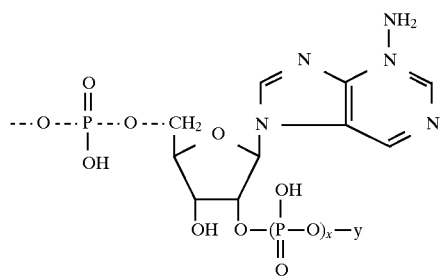

where y can be another group having the structure represented by Formula 2

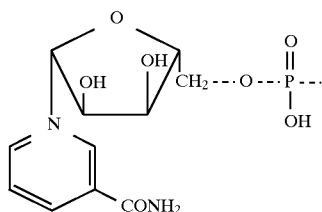
FORMULA 2

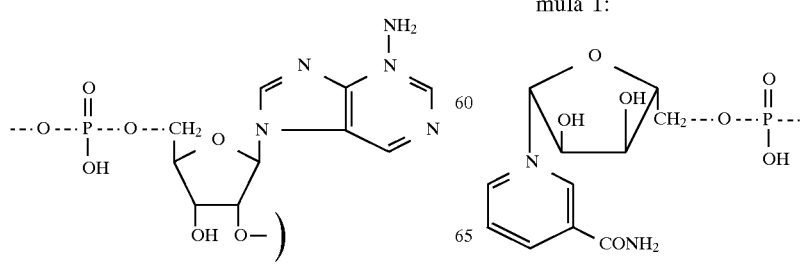

or a group having a structure represented by the structure of

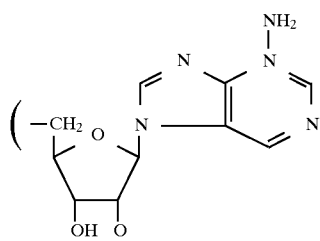
FORMULA 3 and x can be 1, 2, or 3.

2. The method of claim 1 wherein the method further includes selecting the method of administration of the compound of formula 1 from the group consisting of transdermal, subcutaneous, intermuscular, orally, rectally, nasally.

3. The method of claim 1 wherein the method further includes a dosage administered between about 0.05 mg/kg/min to 10.0 mg/kg/min.

4. The method of claim 1 wherein the method further includes administering the preferred dosage via enteric coated orally administered tablets.

5. The method of claim 1 wherein the method further includes administering the dosage intravenously.

6. The method of claim 1 wherein the method further includes administering the compound of Formula 1 together with pharmaceutically acceptable excipients and adjuvants.

7. The method of claim 6 wherein the method further includes administering the medicament is in the form of an orally administered tablet having an enteric coating.

8. The method of claim 1 wherein the method further includes administering the medicament is administered for a period of time of required to achieve sobriety in the inebriated person.

9. The method of claim 1 wherein the method further includes administering the compound of formula 1 to relive the symptoms of acute inebriation.

10. The method of claim 1 wherein the method further includes administering the medicament via the transdermal route of administration.

11. A method of preventing the symptoms associated with alcoholism comprising:

administering to a person deemed in need of preventative therapy, a medically effective, pharmaceutically acceptable form of a compound represented by Formula 1:

FORMULA 1

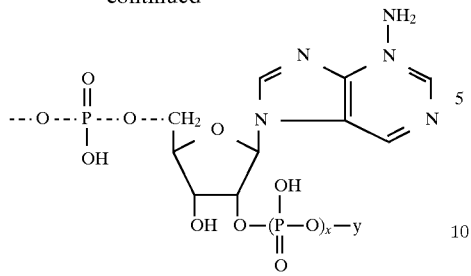

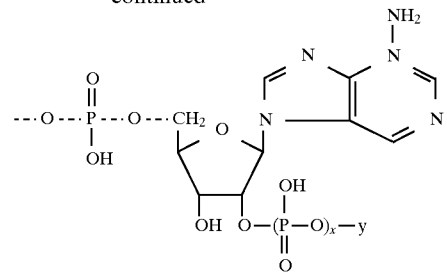

where y can be another group having the structure represented by Formula 2

FORMULA 2

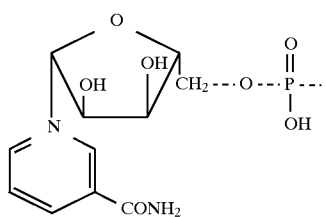

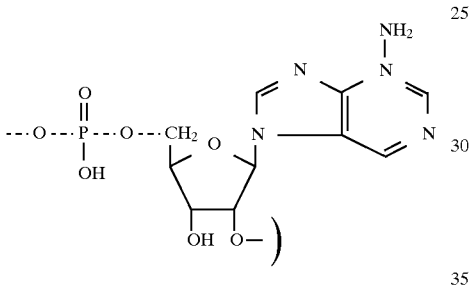

where y can be another group having the structure represented by Formula 2

FORMULA 2

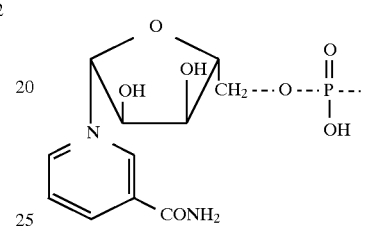

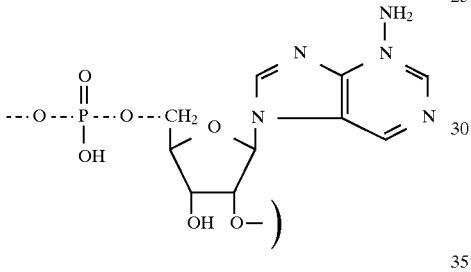

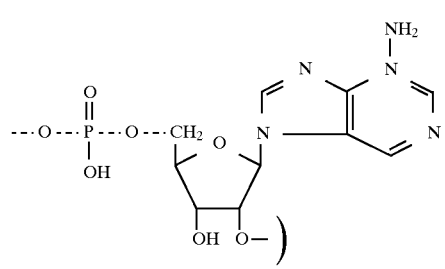

or a group having a structure represented by the structure of

FORMULA 3

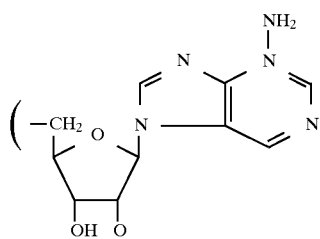

and x can be 1, 2, or 3.

12. A compound presented by Formula 1:

FORMULA 1

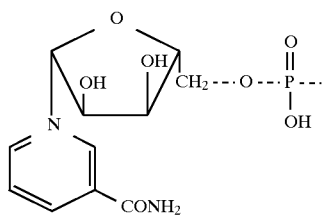

or a group having a structure represented by the structure of

FORMULA 3

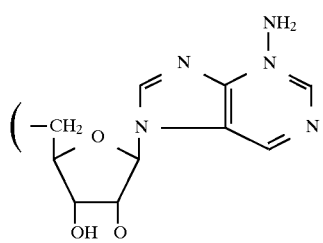

and x can be 1, 2, or 3 including pharmaceutically acceptable salts.

13. The compound of claim 12 wherein Y is represented by Formula 2 and X is 1.

14. The compound of claim 12 wherein Y is represented by Formula 3 and X is 3.

* * * * *